United States Patent [19]

Packard et al.

[11] Patent Number: 4,889,916

[45] Date of Patent: Dec. 26, 1989

[54] PROTEIN LABEL AND DRUG DELIVERY SYSTEM

[75] Inventors: Beverly Packard; Michael Edidin, both of Baltimore; Akira Komoriya, Rockville, all of Md.

[73] Assignee: The Johns Hopkins University, Baltimore, Md.

[21] Appl. No.: 151,186

[22] Filed: Feb. 1, 1988

Related U.S. Application Data

[62] Division of Ser. No. 799,637, Nov. 19, 1985, Pat. No. 4,751,286.

[51] Int. Cl.[4] .............. C07D 311/82; G01N 33/533; A61K 39/395; C07K 15/00
[52] U.S. Cl. ............................. 525/54.1; 530/390; 435/181; 436/532
[58] Field of Search ............. 525/54.1; 530/380, 390, 530/391; 435/181; 436/86, 88, 532

[56] References Cited

U.S. PATENT DOCUMENTS 4,618,492 10/1986 Blattler et al. ................ 424/87

OTHER PUBLICATIONS

Chemical Abstracts, vol. 100, pp. 430–431 (1984), Abstract No. 190020K.

*Primary Examiner*—John Kight
*Assistant Examiner*—Nathan M. Nutter
*Attorney, Agent, or Firm*—Cushman, Darby & Cushman

[57] ABSTRACT

A bridging molecule carrying a drug, or a label such as a fluorophore, which adds across disulfide bonds of molecules, particularly proteins, and methods of manufacturing and using the bridging molecules, are disclosed. The bridging molecule is reactive with sulfhydryl groups formed by the reduction of disulfide bonds of the protein. The functional groups of the bridging molecules are typically —SH groups.

12 Claims, 2 Drawing Sheets

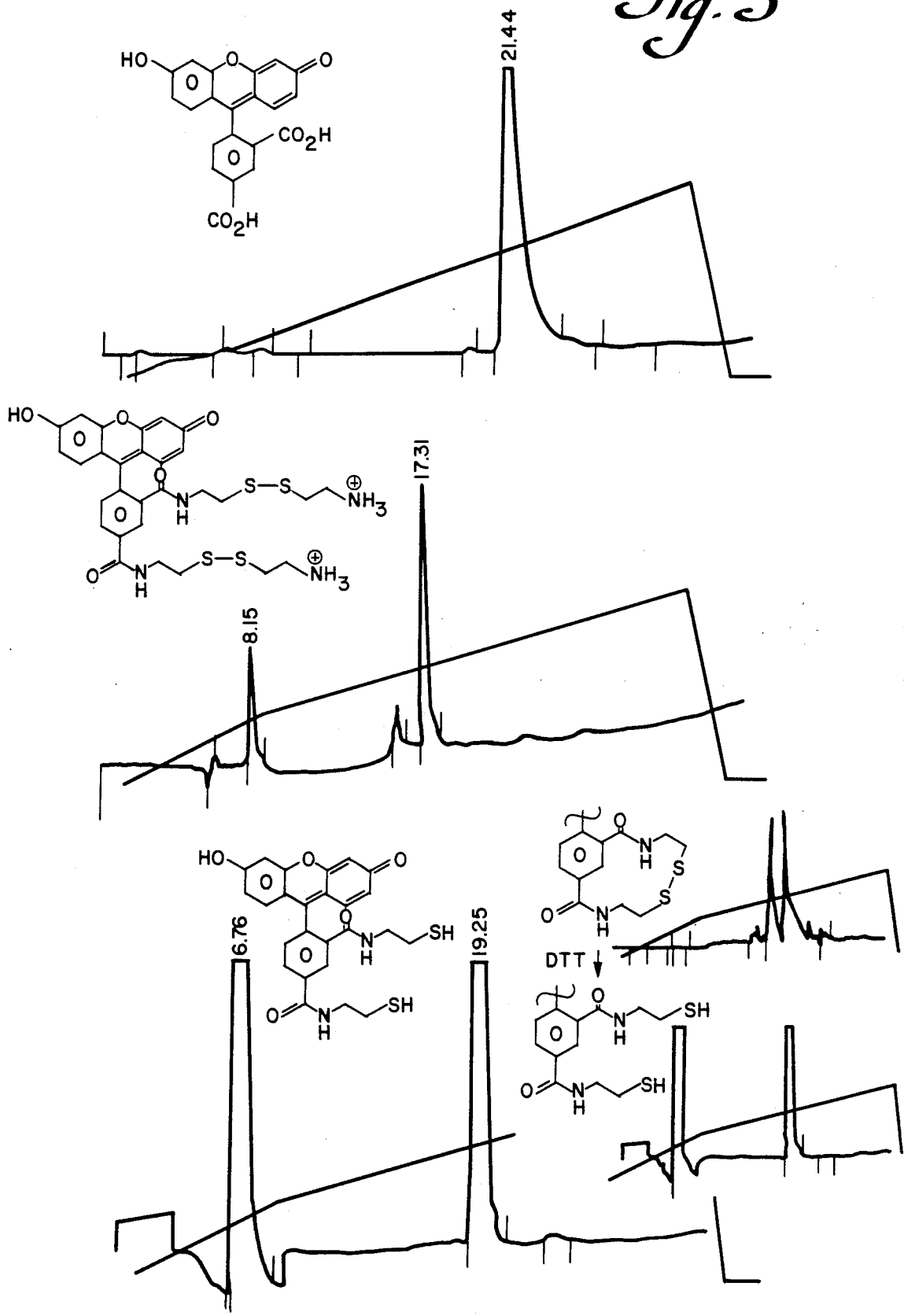

PROTEIN LABEL AND DRUG DELIVERY SYSTEM

The invention described and claimed herein was made by a grant or award from the U.S. Department of Health and Human Services.

This is a division of application Ser. No. 799,637 filed Nov. 19, 1985 and now U.S. Pat. No. 4,751,286.

The present invention relates to a bridging molecule carrying a drug, dye, or a label such as a fluorophore. The bridging molecule adds across the disulfide bonds of molecules, particularly proteins. The invention also relates to methods of manufacturing and using the bridging molecule.

BACKGROUND OF THE INVENTION

Fluorescence spectroscopy of macromolecules is used in many areas of biology. Application of the technique can produce valuable information due to the inherently high sensitivity of fluorescence emission and the abundance of potential labeling targets in cells. Types of questions that can be addressed include the identification of antigens on cell surfaces, the study of subcellular compartmentalization, and the dynamics of macromolecular motion. While many of these applications require only that a molecule be labeled with a fluorescent probe at a sufficiently high level to visualize it, other applications, for example, the measurement of rotational diffusion of membrane proteins, depend critically upon the uniformity of protein labeling and the extent to which the dynamic properties of a fluorescent group accurately reflect the dynamics of the target molecules.

Typically, proteins such as antibodies are labeled on the nucleophilic sites on the surface of the protein, i.e. the amino chain termini and the epsilon-amino groups of lysines, using fluorophores containing reactive groups such as isothiocyanates, triazinates, and sulfonyl chlorides. Additionally, the sulfhydryls of cysteines as well as the carboxyls of aspartic and glutamic acids are potential targets for labeling with fluorophores. Several drawbacks are inherent in all commonly used covalent labeling procedures. First, proteins contain a multitude of comparably reactive groups; thus, labeling of proteins usually results in a population of molecules with a random distribution of label location and substitution level. Unfortunately, many of the labeled sites on a protein exhibit sufficient chemical homogeneity that resolution into distinct species is not readily feasible. Thus, even if the substitution level of fluorophore to protein is 1:1, multiple fluorescent environments may coexist. Hence, if the degree of label incorporation is not uniform, proteins labeled in this manner would not be desirable for use in a quantitative assay since the range of fluorescence signals for a given fixed antigen could vary greatly.

A second drawback is the autonomous rotational motion that a fluorophore may retain relative to the labeled protein molecule. This is a consequence of the fact that the chemical linkage between commonly used fluorophores and proteins is a single covalent bond. For many classes of measurements, this is not a drawback; however if, for example, one uses a fluorescence signal to determine the rotational motion of a protein, the time-dependent polarization may be dominated by the motion of the probe. Thus, the value obtained is probably not a true indicator of the rotational correlation time of the protein.

A third drawback is that the commonly used method of labeling the surface of the protein may result in a modified tertiary structure which can alter the biological activity of the protein.

Generally, in the dye industry, the dye molecule is hydrophobic and associates with the fibrous protein such as hair, wool, silk, etc., in a non covalent complex. A problem associated with this method of coloring materials with dye is that over time the dye fades, as the dye molecules dissociate from the fibrous protein. Other methods of dyeing fibrous proteins include the attachment of the dye molecule to the fibrous protein by a single covalent bond created by alkylation, or using one cysteine group. This process is irreversible.

The drug delivery systems presently used involve attachment of a drug to the surface of a protein such as an antibody creating an antibody conjugate. This method, however, can cause an immune system response since the conjugated antibody is recognized by the body as a foreign molecule.

Molecules with bifunctional groups have been attached to proteins, e.g. where one functional group reacts with a sulfhydryl of the protein while the other reacts with an amino group of the protein. This bifunctional method of modifying the protein, however, is not reversible and can change the tertiary structure of the protein. If only one of the —SH groups of a reduced disulfide bond is reacted, the structural stabilizing influence of the original —S—S bond is lost and the tertiary structure is likely to change.

SUMMARY OF THE INVENTION

A bridging molecule is disclosed having the structure:

wherein A is a group containing a drug, dye or label, which is unreactive with sulfhydryl groups; and X and Y are functional groups such as halides or sulfhydryl groups reactive with sulfhydryl groups formed by the reduction of disulfide bonds of a molecule, particularly a protein, to be bridged.

Methods for synthesizing, and for reacting the bridging molecule with a molecule containing reduced disulfide bonds, are also disclosed. Disulfide bonds interconnect chains of many proteins, and are internal rather than on the surface of the protein. The bridging molecule is designed to rigidly insert a small bridge into a disulfide bond of a protein, thereby rigidly inserting onto the protein, a drug, dye or a label such as chromophores, fluorophores and radioisotopes which are covalently attached to the bridge.

The bridging molecule is designed to preserve the native protein structure. The insertion of the bridging molecule affects the biological activity of an immunoglobulin only slightly if at all. The bridging molecule is homobifunctionally reactive with the sulfhydryl (—SH) groups formed by reduction of the disulfide (—S—S—) bonds of the protein. The functional groups of the bridging molecules are typically —SH groups, but other bifunctional cross-linkers may also be used to rejoin the reduced halves of the —S—S— bond of the protein. If the functional groups are —SH groups, the addition of the bridging molecule is reversible, i.e. the bridging molecule can be dissociated from the protein by reduction. The crosslinking is intra-molecular.

The bridging molecule may bear a label such as: (a) a fluorescent dye, (b) a chromophore, (c) a radioisotope, or alternatively, a reactive amino group, which in turn can be coupled to a label. "Crabescein", a new fluorescent bridging molecule disclosed below, is a preferred embodiment for specific labeling of disulfide containing peptides, where the fluorescence signal comes from a relatively rigid environment. Crabescein reports the rotational correlation time of the immunoglobulin segment to which it is covalently bound.

BRIEF DESCRIPTION OF THE DRAWINGS

FIG. 3 shows the hplc profiles of (a) 5'-carboxyfluorescein (starting material), (b) procrabescein (intermediates), and (c) crabescein (product). Diagonal lines represent a gradient of acetonitrile with the lowest value of 10% and the highest of 90%.

DETAILED DESCRIPTION OF THE PRESENTLY PREFERRED EMBODIMENT

Figure 1:
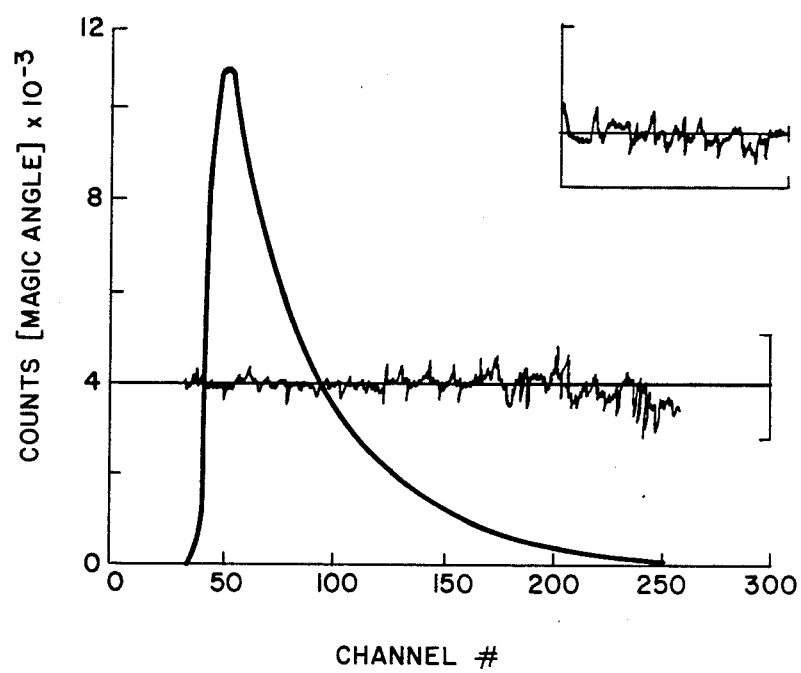
FIG. 1 is the fluorescence decay curve of IgG-crabescein.
Figure 2:
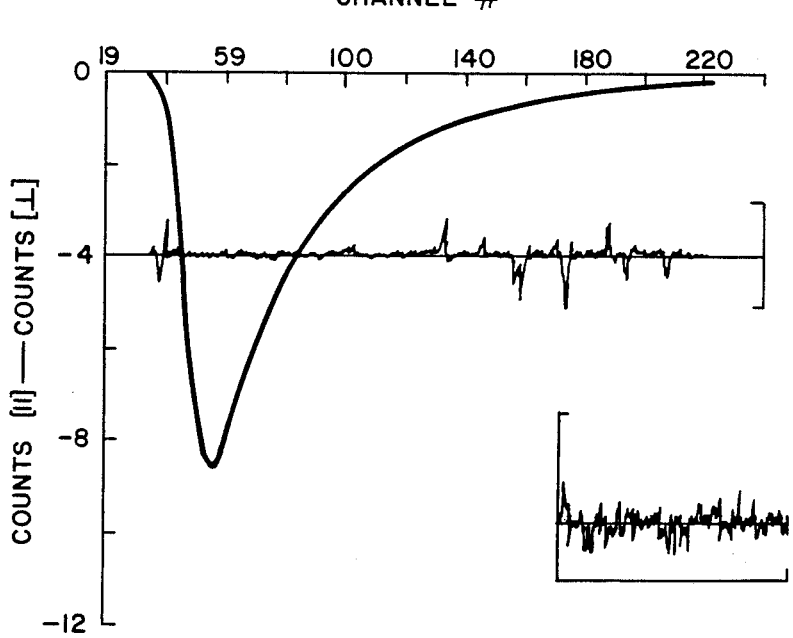
FIG. 2 is the difference curve of IgG-crabescein.

The bridging molecule has the structure:

wherein A is a group containing a drug, dye or label, which is unreactive with sulfhydryl groups; and X and Y are functional groups such as halides or sulfhydryl groups reactive with sulfhydryl groups formed by the reduction of disulfide bonds of a molecule, particularly a protein, to be bridged. For the case of a protein, the bridging molecule has a size permitting reaction with reduced disulfide bonds of the protein.

The bridging molecule can be rigidly attached to a molecule, particularly a protein, in a gentle and site-specific manner. The bridging molecule is targeted to disulfide bonds and achieves its specificity due to the following design elements: (1) disulfides in proteins are relatively limited in number, (2) two attachment sites on the bridging molecule prevent its free rotation, (3) disulfides are located internal to proteins but are still accessible to solvent molecules as well as to other molecules on the size scale of fluorescein, and (4) a disulfide bond that is modified by insertion of a bridging molecule will retain its tertiary structural stabilizing influence.

An advantage of the bridging molecule is that protein conformation is maintained and, in contrast to labeling amino or carboxyl groups, net charge of the molecule is not changed if the group A does not carry a net charge. Since coupling conditions are mild, overall, the labeled molecules more closely approximate their native form than molecules labeled in any other manner. Thus, an antibody is likely to maintain its biological activity.

A further advantage of a preferred embodiment of the invention is that the bridging molecule, which is relatively rigidly attached to the protein by two covalent —S—S— bonds can be easily removed by reduction, i.e. the attachment is reversible.

The above-noted features are in contrast to derivatization by alkylation where there is the risk of alkylating the nucleophile that may be essential for biological and/or enzymatic activity of the protein.

Another embodiment of the bridging molecule of the invention has the formula:

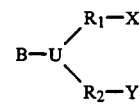

where B is a drug, dye or label, U is a group unreactive with sulfhydryl groups, $R_1$ and $R_2$ are hydrocarbon chains or amide groups, and X and Y are functional groups as described above. In a preferred embodiment, U is nitrogen, and $R_1$ and $R_2$ are alkyl groups, for example —$(CH_2)_{\overline{n}}$, n=1 to 4, or olefinic groups, for example —$(CH_1=CH_1)_{\overline{n}}$, n=1 to 2.

Another advantage of the invention with respect to the use of the bridging molecule as a label is that the motion of the incorporated label is restricted. Fluorescence depolarization can be measured more accurately from such labeled macromolecules than can be measured from molecules whose labels are linked by a single covalent bond. When molecules labeled by the method of the present invention are used in polarization assays, for example, polarization of fluorescence immunoassays, the result is much greater signal to noise ratios.

The invention is exemplified by the modification of a fluorescein derivative, 5'-carboxyfluorescein, by synthesis of a new labeling reagent (bridging molecule), "crabescein", that links fluorescein to proteins in a highly selective manner—across disulfide bridges. An antibody labeled with crabescein, like the same antibody conventionally labeled with fluorescein, stains cells brightly. Conventionally labeled antibodies, however, bear fluorescein at several different sites and the rotation of the fluorophore is faster than that expected for the protein in solution. In contrast, antibodies labeled with crabescein bear the fluorescein label at a single site—across a disulfide in the hinge region of the antibody. Thus, in the case of IgG labeled with the bridging molecule of the present invention, the rotational correlation time of the probe reflects the motion of the $F_c$ region of the IgG.

Crabescein may be synthesized according to the invention by derivatizing the two carboxyls on the phenyl ring of 5'-carboxyfluorescein with two sulfhydryls (—SH). The intermediate is called "procrabescein."

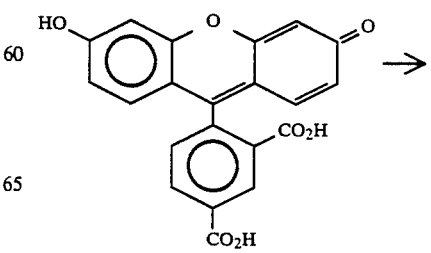

-continued

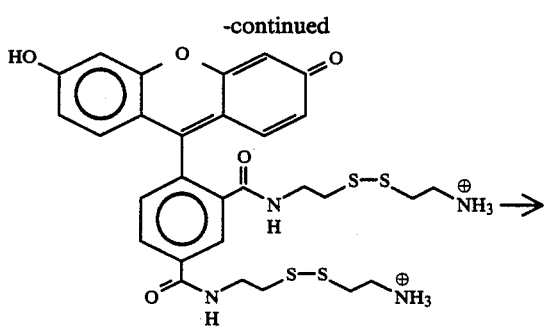

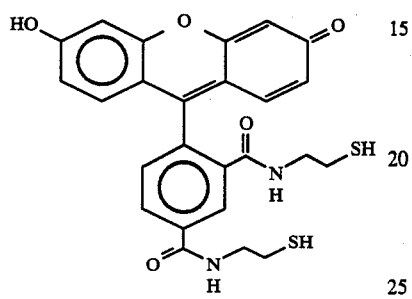

Crabescein under oxidative conditions has a tendency to close its "claw". This can be reversed, i.e., opened by treatment with a reducing agent.

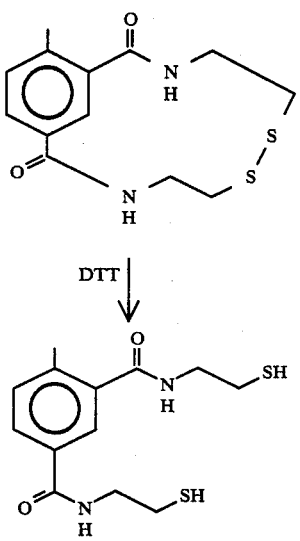

Although any protein having accessible disulfide bonds can be modified with the bridging molecule, an immunoglobulin was chosen as the protein because (1) it has been shown to have a limited number of accessible disulfide bonds and (2) the disulfides of the protein can be reduced without dissociating the heavy and light chains.

Thus, the immunoglobulin was "unzipped" by reduction at a pH of about 8–10 with a reducing agent such as dithiothreitol (DTT) using up to a 10-fold excess of DTT or 2 mercapto ethanol; crabescein was then inserted (using up to a 100-fold excess of crabescein) into the protein by heteromolecular disulfide bond (—S—S—) formation; and the immunoglobulin was zipped back up by reoxidation. This procedure was performed using IgG and IgE at a temperature below the denaturation temperature of the protein.

As noted above, the functional groups X and Y of the briding molecule need not be sulfhydryl groups. If X and Y are halides such as chlorine or bromine on alkyl groups, the briding molecule is joined to the protein by two C-S bonds. The sulfhydryl groups of the protein remaining after the insertion of the bridging molecule, are oxidized or alkylated.

The amino acid sequence analysis of the fluorescent label-containing immunoglobulins indicated that the fluorophore was inserted into the hinge region across the disulfide bond closest to the C2 domain.

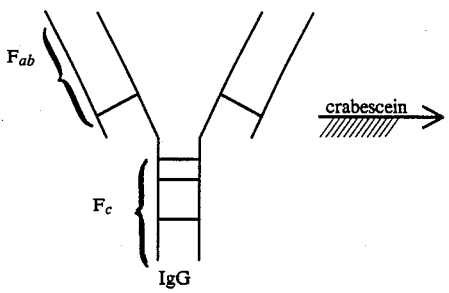

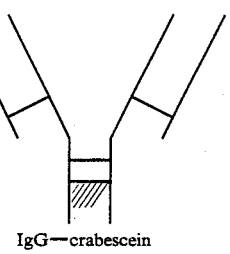

Crystallographic structural analyses of IgGs have shown that unlike the region of the interchain disulfide bond in the $F_{ab}$ segment, below the hinge region there is little interchain interaction between heavy chains. Thus, there is a space in this region large enough for a molecule the size of crabescein to enter and reside in. It has been observed that crabescein preferentially inserts across the disulfide bond closest to this space, specifically across the third (cys-229) disulfide bond in the hinge region (most digital from the $F_{ab}$ arms).

IgG-DTAF, a derivative in which the macromolecule and fluorophore are linked via one point attachments as in the prior art, contains on the average one molecule of fluorescein per IgG. Three decay constants, with none representing more than 56% of the total signal, are required to describe its decay (see Table 1 below). It is not possible to say whether the three lifetimes represent three physically distinct sites or are representative of microheterogeneity of ground or excited states; however, the fact that the species with the lifetime approaching that of free crabescein in solution (ca. 4 nanoseconds (ns)) represents only 14% of the fluorescing species indicates that the protein and the probe are interacting with each other.

IgG-DTAF exhibits two relatively short (0.20 and 14.3 ns) rotational correlation times. The longer one, 14.3 ns, is in the range (14–18 ns) of the short phi which has been ascribed to the V-module flexing at switch peptides in the $F_{ab}$ segment. The four amino termini which exists at the $F_{ab}$ ends are potential labeling sites for DTAF as are other amino groups of the IgG. Thus, the origin of the 14.3 ns is not clear. The subnanosecond phi may report the rapid depolarization due to the antonomous motion of the probe relative to the IgG.

The decay behavior of IgG-crabescein is in sharp contrast to that of IgG-DTAF. The intensity decay of the crabescein derivative is best described by two constants with 32% of the fluorescing species exhibiting 1.22 ns and the remaining 68% showing 4.41 ns. The two lifetimes may be a consequence of the asymmetric location of the claw in crabescein such that the fluorophore has the option of inserting in two different directions. Since IgGs have carbohydrate residues near the site at which carbescein attaches, the fluorophore may report on two quite chemically distinct but physically identical environments.

The amino acid sequence data indicate that the location of crabescein is in the $F_c$ domain of the immunoglobulin. The absence of free sulfhydryls as indicated by the absence of radioactive counts after exposure of the crabescein labeled IgG to $C_{14}$ labeled iodoacetamide, in addition to the ability of the antibody to recognize its antigen on the cell surface, indicates that we are reporting the rotational correlation time of an intact, possibly slightly perturbed $F_c$ domain of a whole IgG.

It is possible that an additional longer rotational correlation time(s) than the 28 ns reported here does exist for the whole IgG. However, due to the relatively short fluorescence lifetime of fluorescein, 28 ns is near the limit of a probe with a 4 to 4.5 ns lifetime.

An advantage of the dye carrying embodiment of the invention is that the bridging molecules, if inserted as bifunctional —SH reactive molecules, can be easily removed by reduction of the modified disulfide bridge. Thus the addition of the bridging molecule is reversible. This property can be used to make stable (attached by two covalent bonds), i.e. unlikely to fade, but quickly removable dyes for hair or other proteins.

The drug delivery system embodiment of the invention involves a bridging molecule of the structure:

where D is a drug carrying molecule and X and Y are functional groups reactive with sulfhydryl groups formed by the reduction of disulfide bonds of a protein, particularly an antibody. The conjugate formed by the addition of this bridging molecule to an antibody has virtually the same tertiary structure as the unmodified antibody since the drug is attached internally to the antibody, thus avoiding the potentially severe toxicity problems associated with drug delivery systems where the drug is attached on the surface of the antibody. Further, since the attachment of the bridging molecule is internal in the antibody, its biological activity is affected minimally if at all.

As an example, a bridging molecule containing a toxin to kill a tumor cell or cancer cell is attached across the reduced disulfide bonds of a monoclonal antibody or polyclonal antibody which has as its target, a tumor or cancer cell. The antibody enters the cell, and as it is degraded, the toxin is released.

Diphtheria toxin or a molecule containing radioactive element(s) are examples of toxins which could be attached to the bridging molecule.

In addition to use of an antibody as the carrier of the toxin carrying molecule, a hormone could be used.

The bridging molecules in another embodiment of the invention can be modified to contain rigid spacer arms within the bridge. Selective insertion of these spacer molecules into an antibody, such as the $F_{ab}$ region of IgG, can alter its affinity. The insertion of a bridging molecule across the reduced disulfide bonds in the $F_{ab}$ region would require a molecule of small enough size to reach those reduced disulfide bonds. Such alterations result in lower affinity and greater ease of elution of antigens from modified antibody columns than from columns using unmodified antibodies. Insertion of a spacer molecule into other proteins can also alter their properties.

A still further embodiment of the invention involves the artificial addition of disulfide bonds or pairs of sulfhydryl groups to molecules not already having disulfide bonds, thus permitting the attachment of the bridging molecule of the invention. The addition of disulfide bonds or pairs of sulfhydryl groups creates the advantages noted above with respect to proteins, for the molecules with artificially added disulfide bonds.

For the case of proteins which do not have an amino acid sequence containing a modification site, i.e. disulfide bond(s) or pair(s) of sulfhydryl groups, and/or which have a tertiary structure that makes the potential modification site inaccessible, disulfide bond(s) or pair(s) of sulfhydryl groups can be introduced into the amino acid sequence through the recombinant DNA technique, or chemical modification by either direct addition of the disulfide bond(s) or pair(s) of sulfhydryl groups or, endymatically.

The invention will be more fully understood from the examples which follow.

EXAMPLE I

(1) Methods (a) Synthesis of Crabescein

5'-Carboxyfluorescein ($3.7 \times 10^{-5}$ mole) (Calbiochem), cystamine (Sigma Chemicals Co.), diisopropylcarbodiimide and 1-hydroxybenzotriazole (Aldrich Chemical Co.) were dissolved in dimethylsulfoxide (571 μl) at a molar ratio of 1:10:40:40, respectively, and the pH was adjusted to 10. After mixing at room temperature for ten minutes, the solution was diluted with a 0.1% trifluoroacetic acid (tfa)-containing mixture of water and acetonitrile in a volume ratio of 9:1, respectively. The precipitate (mostly urea) was removed by centrifugation. The intermediate product, "procrabescein", was isolated by reverse phase chromatography hplc (Waters Associates) using a microbondapak CN column (7.8 mm × 30 cm) (Waters Associates). An elution gradient which ran from an initial composition of 10% (v/v) acetonitrile in water to a final composition of 90% (v/v) acetonitrile in water, with 0.1% tfa (v/v) present throughout.

After removal of the hplc solvents (Baker and Aldrich Chemical Cos.) by lyophilization, the ninhydrin-positive compound was dissolved in an aqueous solution containing 50% ethanol containing dithiothreitol (DTT) (Sigma Chemical Co.) in 10-fold molar excess over the procrabescein. The reduced product was separated by the same reverse phase conditions used above.

Proton nuclear magnetic resonance (nmr) (Varian LX-400 MHz), ultraviolet-visible (uv-vis) (Varian Cary 219), and mass spectra (Hewlett-Packard model 5980A) of the final product, crabescein, were then taken.

(b) Incorporation

A mouse monoclonal antibody IgG2a, was produced by a murine cell line (gift of Roger Kennett of the University of Pennsylvania). This antibody is denoted "KE-2" herein. KE-2 cells were grown in Eagle's minimal essential medium with 10% fetal calf serum. The IgG was purified from spent medium by adsorption to affi-gel protein A (Biorad) and eluted according to the MAPS (Biorad) procedure.

(i) Formation of IgG-Crabescein

Antibody KE-2, to the human major histocompatibility antigens, HLA-A,B,C, was dissolved in phosphate buffered saline (PBS) (pH 7.4) at a concentration of 1 mg/ml. To this solution were added a ten-fold molar excess of DTT (to reduce or "unzip" the IgG) and a five-fold molar excess of ethylenediaminetetraacetic acid (EDTA) to chelate (eliminate) any metal ions which could react with the sulfhydryls formed. The pH was adjusted to 10 and the solution was incubated at 37° C. for 30 minutes.

A 100-fold molar excess of crabescein was then added and the incubation was continued at 37° C. for an additional 10 minutes to form the IgG-crabescein.

Oxygen gas was then bubbled through the solution and the pH was dropped to 5.5; the solution was kept at 37° for ca. 22 hours (to oxidize or "zip up" the IgG).

The reaction mixture was then chromatographed on a Biogel P10 column with PBS at pH 7.4 as the eluting buffer. The void volume peak was collected and further chromatographed on an hplc using a TSK g3000sw column (LKB instruments, 7.5×600 mm) with an aqueous elution buffer composed of 150 mM NaCl and 15 mM phoshphate at pH 7 and a flow rate of 0.8 ml/min. The labeled antibody was collected, dialyzed against PBS (pH 7.4), and stored at −20° C. The purity of the concentrated sample was assessed using gel permeation chromatography with the TSK g3000sw column; a single peak of the same retention time as the unlabeled antibody was observed and no free label was present in the sample.

(ii) Formation of IgG-DTAF

KE-2 IgG was also labeled with 5-4,6-dichloro-s-triazin-2-yl)aminofluorescein (5-DTAF) (Molecular Probes). Conditions used were: 9 moles of DTAF per IgG in PBS at pH 9 for two hours at room temperature. Separation and purification procedures were similar to those used for crabescein labeling.

The number of fluorophores per IgG was determined by measuring the absorbances at 496 and 280 nm, and taking their ratio using an extinction coefficient of 8.1×10(4) M(−1) at 496 nm and an absorbance of 1.0 O.D. for 1 mg/ml of a 150 kdalton protein at 280 nm.

(c) Trypsin Fragmentation

In order to insure that there would be no interchange between crabescein and any incompletely oxidized disulfide bonds of the protein, the IgG-labeled with crabescein was exposed to a 10,000-fold excess of $C_{14}$-iodoacetamide (DuPont) in PBS (pH 7.4) for 30 minutes at 37° C., followed by addition of cold acetamide (equal amount) and chromatographed on a PD10 column with 10% acetic acid in the elution buffer. Two column volumes were collected and the eluant was counted for $C_{14}$; no counts above background were detected in the protein peak.

The location of crabescein in the immunoglobulin was determined from the analysis of tryptic IgG fragments. IgG-crabescein (ca. 200 μg) was digested with TPCK-trypsin (Worthington Biochemical Chemical Co.) in a 1% (w/v) ammonium bicarbonate buffer containing 10 mM calcium chloride (pH 8.1) at 37° C. for three hours in the dark. The ratio of trypsin to antibody by weight was 1:20 with a final volume of 200 μl. The pH of the final digestion solution was adjusted to 9 with a dilute ammonium hydroxide solution. The digestion was terminated by the addition of 100 μl. of 0.1%% (v/v) trifluoroacetic acid.

The trypsin digestion sample was chromatographed on a Water's hplc equipped with a Gilson fluorescence detector (model 121) with excitation and emission filters of 496 and 520 nm, respectively, in series with an absorption detector set at 220 nm. A SynChrom C4 column (3.5 mm×300 mm) was used with water and acetonitrile containing 0.1% (v/v) trifluoroacetic acid in the eluting buffer. The gradient was: 10% acetonitrile for 10 minutes followed by a linear gradient to a final composition of 50:50::acetonitrile:water over 40 minutes at a flow rate of 0.8 ml/min.

The amino acid sequence of the crabescein-containing fragment was determined using an Applied Biosystems gas phase protein sequencer model 440.

(d) Fluorescence Measurements

Time-resolved fluorescence decay measurements were made using a Yg-Nd pulse laser (Spectra-Physics) driving a dye laser which contained rhodamine 6G. The excitation wavelength was 313 nm and emission was observed at 522 nm. The temperature of the cuvette was 28° C. The system had a repetition rate of 800 kHz with a full width at half maximum of 850 ps. One data file was generated with photon collection at the magic angle (54.7 degrees), a second with a polarizer parallel to the exciting beam and a third with the polarizer perpendicular. Data were analyzed by nonlinear least square methods. Examples of decay and difference curves are shown in FIGS. 1 and 2 respectively.

Steady state anisotropies were measured in an SLM model spectrofluorometer.

(e) Cell Staining

VA-2 cells, a line of SV-40 transformed human fibroblasts, were incubated with the IgG-crabescein or IgG-DTAF at ca. 0.10 pM for 30 minutes on ice. The cells were then washed with cold PBS and examined under a fluorescence microscope.

(2) Results (a) Synthesis of Crabescein

The final product contains a claw, was made in Maryland, and was derived from fluorescein; therefore, it was named crabescein. The intermediate product was named "procrabescein".

The starting material, procrabescein, and crabescein all exhibited the typical uv-visible spectrum of fluorescein, i.e., a major peak at 496 nm with a shoulder at shorter wavelengths in PBS containing 1% (ethanol (v/v).

The nmr spectra of procrabescein and crabescein showed the addition of the methylene groups with split triplets between 2.5 and 3.6 ppm downfield from tetramethylsilane (TMS), slight downfield shifts of the two aromatic protons on the carbons adjacent to the derivatized carbonyls, and two peaks due to the two amide protons. The spectrum of procrabescein also had a broad peak at ca. 6.2 ppm which integrated for the six amine protons. The spectrum of crabescein showed half the number of methylene protons between 2.5 and 3.6 ppm as procrabescein and the loss of the amine protons; these are consistent with the loss of two aminoethylenemercapto moieties upon reduction. The addition of a peak at 7.2 ppm, which disappeared in the presence of deuterated water, indicated the exchangeable protons were the sulfhydryls of crabescein. The mass spectrum of crabescein showed a parent molecular ion of 430 which indicated that the parent ion had undergone a rearrangement which resulted in the loss of the two sulfurs.

(b) Incorporation Of Dye Molecules

By absorption spectroscopy ca. 0.30–0.42 molecule crabescein and 1.4 molecule DTAF were incorporated per IgG.

(c) Typsin Fragmentation

Only one major fluorescent peak was obtained by reverse phase chromatography from the three hour trypsin digestion of IgG-crabescein. The retention time for the major fluorescence-containing peak (95% of the total fluorescence) was 31 minutes; after collection it was further digested with trypsin and its retention time was not altered. The amino acid sequence of the 31 minute peak was analyzed twice using two separate digestion samples by a gas phase sequencer. Nine Edman cycles were performed and the amino acid sequence obtained was consistent with the sequence of a tryptic fragment of mouse IgG2a heavy chain at the hinge region: C-P-A-P-N-L-L-G-G (with underlined letters indicating the obtained sequence). The levels of phenyl hydrodantoin (PTH)-derived amino acids analyzed ranged from 27 to 7 pmoles. The fluorophone is inserted into the third disulfide bond (cysteine-229 of mouse IgG2a) in the hinge region.

(d) Fluorescence Data

As shown in Table 1, the decay of crabescein's fluorescence in PBS (pH 7.4) was monoexponential with a lifetime of 4.05 ns. Its steady state anisotropy (excitation wavelength=331 nm., emission wavelength=522 nm.) was −0.01.

IgG-DTAF had three lifetime: 0.27 ns, 1.63 and 3.98. Its steady state anisotropy was −0.05 and two rotational correlation times of 0.20 ns and 14.3 were measured.

In contrast, IgG labeled with crabescein has a single rotational correlation time of 26.8 ns, and showed two decay constants of 4.41 and 1.22 ns (see FIG. 1), and a steady state anisotropy of −0.07.

TABLE 1

| dy State Anisotropy | Rotational Correlation Time (ns) | Decay Constants (ns) | Stea |
|---|---|---|---|
| Crabescein −0.01 | | 4.05 | |
| IgG-DTAF −0.05 | (a) 0.20 (b) 14.3 | (a) 0.27 (b) 1.63 (c) 3.98 | |
| IgG-crabescein −0.07 | 26.8 | (a) 1.22 (b) 4.41 | |

(e) Cell Staining

Va-2 cells, stained with IgG-crabescein, IgG-DTAF, and Fab-crabescein, showed complete outlines of their entire surfaces. All fluorescence was blocked by preincubation with unlabeled antibody.

EXAMPLE II

Using crabescein as synthesized in Example I, IgE-crabescein was formed using a procedure similar to that described in Example I. By absorption spectroscopy, ca. 1 molecule crabescein was incorporated per IgE.

While the present invention has been illustrated by detailed descriptions of preferred embodiments thereof, it will be obvious to those skilled in the art that various changes in form and detail can be made therein without departure from the true scope of the invention. For that reason, the invention must be measured by the claims appended and not by the foregoing preferred embodiments.

What is claimed is:

1. A method of conjugating a protein with a bridging compound having the formula

wherein X and Y comprise separate functional groups reactive with sulfhydryl groups formed by reduction of disulfide bonds of a protein molecule and A comprises a drug, dye or label portion which is unreactive with sulfhydryl groups, said method comprising the steps of:
 (a) reducing the disulfide bonds of said protein;
 (b) reacting the bridging compound across the reduced disulfide bonds of said protein; and
 (c) oxidizing or alkylating the reduced disulfide bonds remaining after step (b).

2. A method as in claim 1 wherein all the steps are carried out at between room temperature and the denaturation temperature of said protein.

3. A method as in claim 1 wherein the reacting step includes the step of adding about a 100-fold excess of the bridging compound to said protein.

4. A method as in claim 3 wherein the reacting step includes the steps of incubating the bridging compound-protein mixture for about 10 minutes.

5. A method as in claim 1 wherein the oxidizing step includes the steps of bubbling oxygen gas through the solution, and dropping the pH to about 5.5.

6. A method as in claim 1 wherein the reducing step includes the step of reducing the disulfide bonds with dithiothreitol.

7. A method as in claim 1 wherein the reducing step includes the step of reducing the disulfide bonds with 2 mercapto ethanol.

8. A method as in claim 1 wherein the reducing step includes the step of mixing dithiothreitol with said protein at a ratio of from 1:1 to 10:1.

9. A method as in claim 1 wherein the reducing step includes the step of adding an excess of ethylenediaminetetraacetic acid.

10. A method as in claim 1 wherein the reducing step includes the step of adjusting the pH to about 8–10 and incubating for about 30 minutes.

11. A method as in claim 10 wherein the oxidizing step includes the step of keeping the solution at about room temperature for about 22 hours.

12. A method according to claim 1 where X and Y are halogen or sulfhydryl.

* * * * *